US009693731B2

United States Patent
Ichikawa (10) Patent No.: US 9,693,731 B2
(45) Date of Patent: Jul. 4, 2017

(54) ELECTRONIC DEVICE

(71) Applicant: CASIO COMPUTER CO., LTD., Shibuya-ku, Tokyo (JP)

(72) Inventor: Kenzo Ichikawa, Kokubunji-shi (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 0 days.

(21) Appl. No.: 14/885,302

(22) Filed: Oct. 16, 2015

(65) Prior Publication Data

US 2016/0174399 A1 Jun. 16, 2016

(30) Foreign Application Priority Data

Dec. 12, 2014 (JP) ................................. 2014-251388

(51) Int. Cl.

| H05K 1/18 | (2006.01) |
|---|---|
| A61B 5/00 | (2006.01) |
| A61B 5/0245 | (2006.01) |
| A61B 5/01 | (2006.01) |
| A61B 5/024 | (2006.01) |

(52) U.S. Cl.
CPC ............... *A61B 5/681* (2013.01); *A61B 5/01* (2013.01); *A61B 5/024* (2013.01); *A61B 5/0245* (2013.01); *H05K 2201/051* (2013.01); *H05K 2201/056* (2013.01)

(58) Field of Classification Search
None
See application file for complete search history.

(56) References Cited

U.S. PATENT DOCUMENTS

| 7,460,085 | B2 | 12/2008 | Ishii | |
|---|---|---|---|---|
| 7,639,571 | B2 * | 12/2009 | Ishii | G04G 9/02 368/223 |
| 7,722,245 | B2 * | 5/2010 | Baba | G04G 17/08 368/281 |
| 8,072,765 | B2 * | 12/2011 | Yumoto | G02F 1/13452 361/749 |
| 8,482,909 | B2 * | 7/2013 | Douglas | A44C 5/0015 361/679.03 |
| 8,525,613 | B2 * | 9/2013 | Kato | H05K 1/0225 333/238 |
| 8,773,847 | B2 * | 7/2014 | Byun | H04B 1/385 361/679.03 |
| 9,131,039 | B2 * | 9/2015 | Behles | H01L 41/0475 |
| 9,185,802 | B2 * | 11/2015 | Matsuda | H05K 1/142 |

(Continued)

FOREIGN PATENT DOCUMENTS

| JP | 2000209319 A | 7/2000 |
|---|---|---|
| JP | 2005250442 A | 9/2005 |

(Continued)

*Primary Examiner* — Xanthia C Cunningham
(74) *Attorney, Agent, or Firm* — Holtz, Holtz & Volek PC (57) ABSTRACT

An electronic device including a body case which has an accommodating section at least partially in a curved shape, a frame which has a first frame section and a second frame section having a width shorter than a width of the first frame section, and is accommodated in the accommodating section, and a circuit board which is accommodated in the accommodating section so as to be laminated on the frame, and provided so as not to overlap with the second frame section when viewed from a laminated direction of the frame.

13 Claims, 6 Drawing Sheets

(56) References Cited

U.S. PATENT DOCUMENTS

| | | | | |
|---|---|---|---|---|
| 9,190,720 B2* | 11/2015 | Shedletsky | ............... | H01Q 1/38 |
| 2006/0202618 A1 | 9/2006 | Ishii et al. | | |
| 2008/0130421 A1* | 6/2008 | Akaiwa | .................... | G04G 9/00 |
| | | | | 368/82 |
| 2010/0271789 A1* | 10/2010 | Dubois | ................ | H05K 1/0275 |
| | | | | 361/749 |
| 2014/0192483 A1* | 7/2014 | Dangler | ............... | H05K 1/0209 |
| | | | | 361/695 |
| 2015/0017818 A1* | 1/2015 | Lin | ........................ | H05K 1/028 |
| | | | | 439/31 |
| 2015/0136448 A1* | 5/2015 | Sasaki | ................. | H05K 1/0281 |
| | | | | 174/251 |
| 2015/0192903 A1* | 7/2015 | Vondle | ................... | G04G 17/08 |
| | | | | 368/317 |
| 2015/0249297 A1* | 9/2015 | Ng | ......................... | H05K 3/303 |
| | | | | 439/159 |
| 2015/0373830 A1* | 12/2015 | Miyagawa | ............. | H05K 1/028 |
| | | | | 174/520 |
| 2015/0378391 A1* | 12/2015 | Huitema | ................ | G06F 1/163 |
| | | | | 361/679.03 |

FOREIGN PATENT DOCUMENTS

| | | |
|---|---|---|
| JP | 2007075201 A | 3/2007 |
| JP | 2007078670 A | 3/2007 |

* cited by examiner

VIEWED FROM X DIRECTION

FIG. 1C

VIEWED FROM Y DIRECTION

VA-VA CROSS SECTION

FIG. 5B

VB-VB CROSS SECTION

FIG. 5C

VC-VC CROSS SECTION

ELECTRONIC DEVICE

CROSS-REFERENCE TO RELATED APPLICATION

This application is based upon and claims the benefit of priority from the prior Japanese Patent Application No. 2014-251388, filed Dec. 12, 2014, the entire contents of which are incorporated herein by reference.

BACKGROUND OF THE INVENTION

1. Field of the Invention

The present invention relates to an electronic device applicable in a so-called wearable terminal that is worn on the body of a user.

2. Description of the Related Art

In recent years, the development and commercial production of wearable terminals which can provide useful information have been actively advanced. While worn on the body during exercise or in daily life, various kinds of biological information and physical information can be acquired. For example, Japanese Patent Application Laid-Open (Kokai) Publication No. 2007-075201 discloses an aerobic exercise retaining device having a wristwatch type appearance which detects cardiac rate and movement speed while mounted on a user's wrist and notifies the user of various kinds of information based on that detected reference data via a notification means or a display section.

Wearable terminals such as this are used by being directly worn on a part of a human body, such as a wrist or an arm. Accordingly, they are desired by the market and users to be thin with light weight and have a shape with a curvature conforming to a part where they are worn. In addition, in health-conscious boom and sport boom in recent years, high design quality and functionality are desired for wearable terminals as well as sportswear, goods, training machines, and the like. For example, Japanese Patent Application Laid-Open (Kokai) Publication No. 2007-078670 discloses a portable device having an outer appearance of a thin stylish wristband type, which provides various information such as a time and timing information via a display panel provided by being curved conforming to a wrist or an arm where the device is worn.

In a wristband-type wearable terminal such as this, in order to achieve an outer shape having a curvature conforming to a part where it is worn, various electronic components and structural members incorporated therein are required to be thin and have a curved structure or a structure corresponding to a curve. Also, along with an increase in the functionality of the wearable terminal, various electronic components and the like are required to be incorporated.

However, this electronic device having a thin curved shape has following problems. For example, by the use of a flexible printed circuit board (FPC), an inner structure conforming to a curved shape can be achieved so as to actualize an electronic device having a thin curved shape. However, it is difficult to ensure strength that can be resistant to force externally applied at the time of manufacturing or using the electronic device.

In order to solve this problem, the rigidity of an exterior member thereof is increased in one method, and a reinforcing member is provided inside thereof in another method. However, in cases where components and members constituting an electronic device are assembled to have a curved shape with a specific curvature, the peripheral lengths of components arranged overlapping with or adjacent to each other may be subtly changed, or variation at the time of manufacture of the components and members and work variation when the components and members are assembled at the time of manufacturing an electronic device may occur, whereby components, a component and a member, or members easily come contact with each other.

Also, the electronic device in a thin curved shape has another problem in that contact due to a dimensional difference occurring from warpage or deformation by external forces is difficult to be avoided. Due to these variations or the occurrence of a dimensional difference, damage, exfoliation, and the like of a component or member may occur, which may significantly affect the product quality.

The present invention has been conceived in light of the above-described problems. An object of the present invention is to provide an electronic device whose product quality is favorable even if manufacture variation, work variation at the time of assembling, or a dimensional difference due to warpage or deformation occurs to a component or member that is mounted in a device having a thin curved shape.

SUMMARY OF THE INVENTION

In accordance with one aspect of the present invention, there is provided an electronic device comprising: a body case which has an accommodating section at least partially in a curved shape; a frame which has a first frame section and a second frame section having a width shorter than a width of the first frame section, and is accommodated in the accommodating section; and a circuit board which is accommodated in the accommodating section so as to be laminated on the frame, and provided so as not to overlap with the second frame section when viewed from a laminated direction of the frame.

According to the present invention, the occurrence of damage, exfoliation, and the like of a component or member to be mounted in a device having a thin curved shape can be inhibited, and favorable product quality can be achieved.

The above and further objects and novel features of the present invention will more fully appear from the following detailed description when the same is read in conjunction with the accompanying drawings. It is to be expressly understood, however, that the drawings are for the purpose of illustration only and are not intended as a definition of the limits of the invention.

DETAILED DESCRIPTION OF THE PREFERRED EMBODIMENTS

Hereafter, an embodiment of the electronic device according to the present invention will be described in detail. Here, the present invention has been applied in a wristband-type or bracelet-type electronic device that is worn on a wrist of a human body.

Figure 1A:
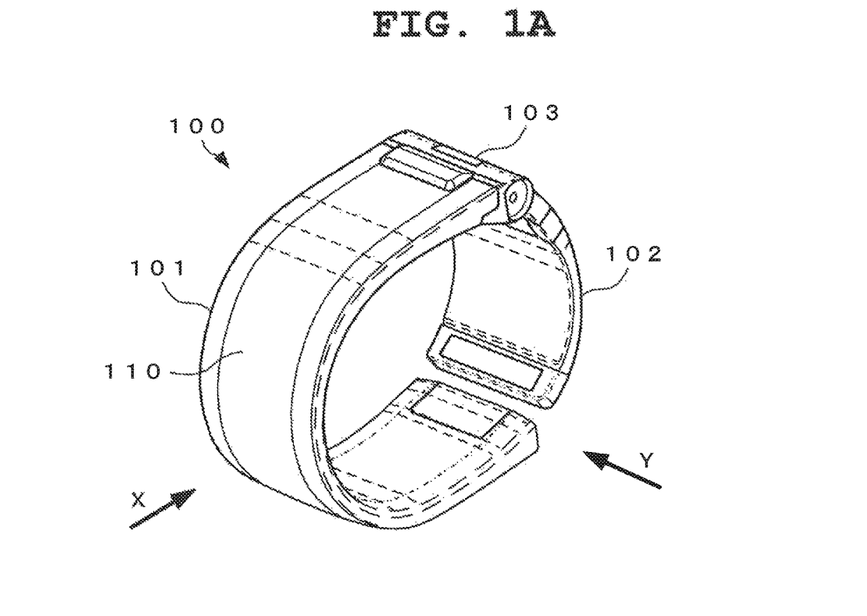
FIG. 1A to FIG. 1C are schematic structural diagrams showing an embodiment of an electronic device according to the present invention.
Figure 1B:
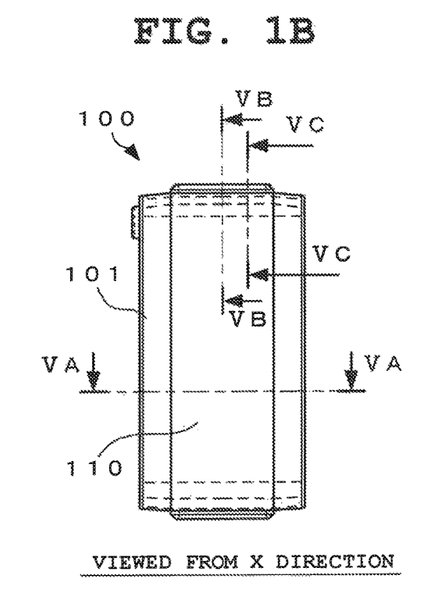
Figure 1C:
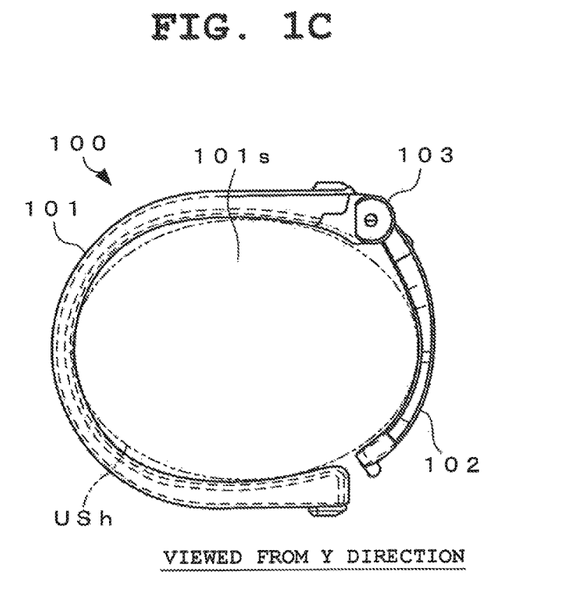
Figure 2A:
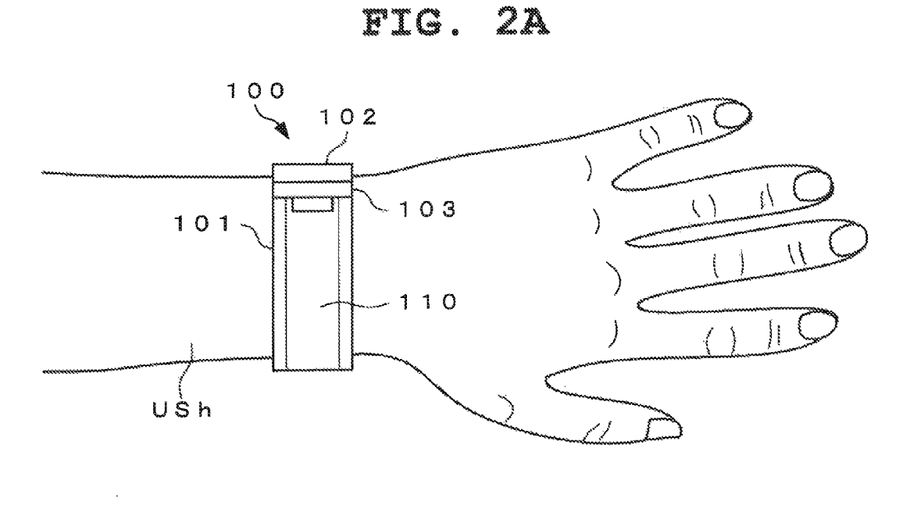
FIG. 2A and FIG. 2B are schematic diagrams showing an example of the electronic device according to the embodiment when it is worn on a human body.
Figure 2B:
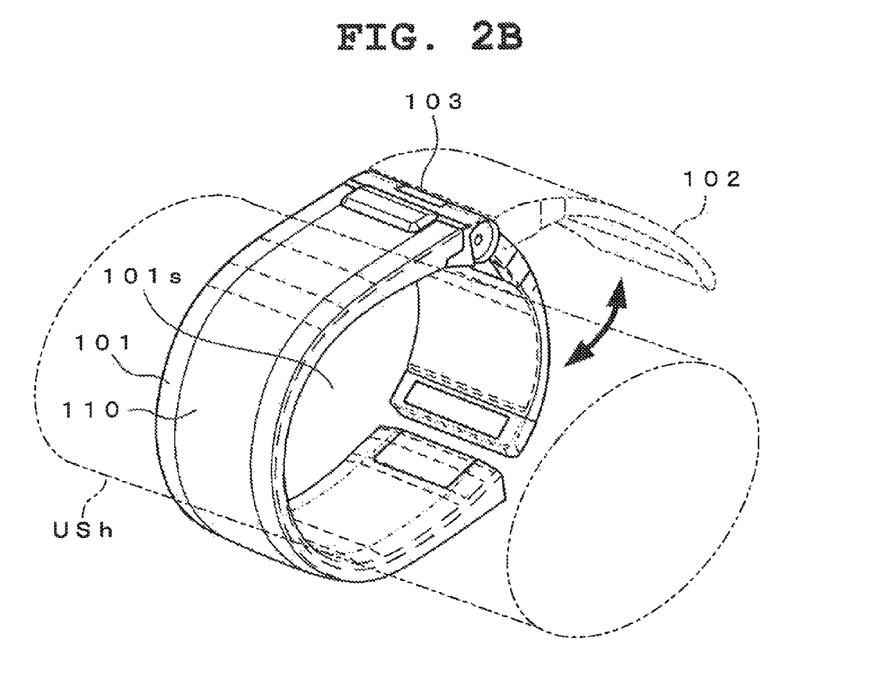
Figure 3:
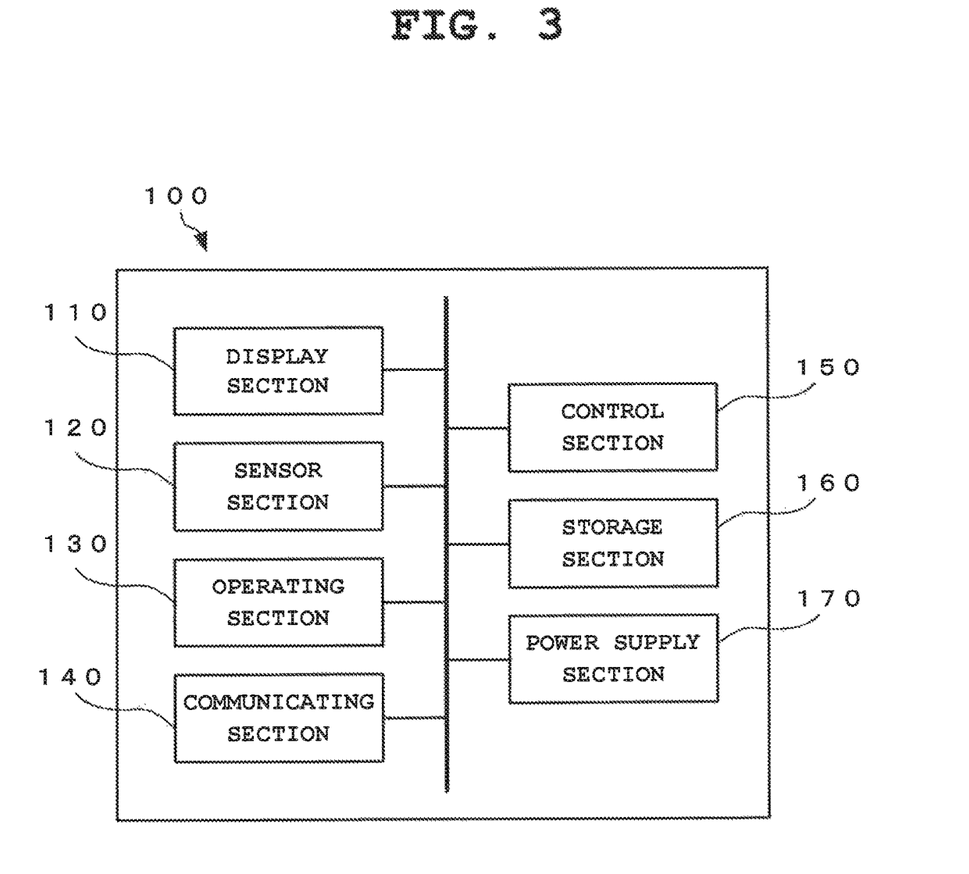
FIG. 3 is a schematic block diagram showing the functional structure of the electronic device according to the embodiment.

FIGS. 1A and 1B are schematic structural diagrams showing the embodiment of the electronic device according to the present invention. FIG. 1A is a schematic perspective view of the structure of the outer appearance of the electronic device according to the present embodiment, and FIG. 1B is a front view of the electronic device shown in FIG. 1A when viewed from a diagonally forward left direction (arrow X direction). FIG. 1C is a side view of the electronic device shown in FIG. 1A when viewed from a diagonally forward right direction (arrow Y direction). FIGS. 2A and 2B are schematic diagrams showing an example of the electronic device according to the present embodiment when it is worn on a human body. FIG. 3 is a schematic block diagram showing the functional structure of the electronic device according to the present embodiment.

(Structure of Outer Appearance)

The electronic device 100 according to the embodiment of the present invention has an outer appearance mainly including, for example, a device body 101 having a curved shape and an opening/closing section 102 rotatably provided on the device body 101, as shown in FIG. 1A to FIG. 1C.

Specifically, the device body 101 is structured by a substantially band-shaped member being curved with a predetermined curvature in a longitudinal direction so as to have a substantially U shape or a substantially C shape when viewed from a side surface side (the arrow Y direction in FIG. 1C), as shown in FIG. 1A to FIG. 1C. On one end of the device body 101 in the longitudinal direction (end portion on the upper side in FIG. 1A and FIG. 1C), a rotating section 103 including a rotating shaft is provided.

The opening/closing section 102 is constituted by a substantially band-shaped member, and its one end (end portion on the upper side in FIG. 1A and FIG. 1C) is connected to the device body 101 via the rotating section 103, as shown in FIG. 1A and FIG. 1C. By the opening/closing section 102 rotating with the rotating shaft of the rotating section 103 as a supporting point (center), the other end (end portion on the lower side in FIG. 1A and FIG. 1B) of the opening/closing section 102 is changed between a closed state (indicated by solid lines in FIG. 2B) of being adjacent to or in close contact with the other end (end portion on the lower side in FIG. 1A and FIG. 1C) of the opening/closing section 101 and an opened state (indicated by two-dot-chain lines in FIG. 2B) of being away therefrom by a predetermined length or more.

(Worn State Example)

In the electronic device 100 having the above-described structure, the opening/closing section 102 is rotated with respect to the device body 101 with the rotating shaft of the rotating section 103 as a supporting point, and thereby enters the opened state where the device body 101 and the other end of the opening/closing section 102 are away from each other, as indicated by the two-dot-chain lines in FIG. 2B. As a result, an inner mount space 101s inside the curved portion of the device body 101 is opened, and thereby allows the electronic device 100 to be worn on or removed from a wrist USh. Then, in the open state where the device body 101 and the other end of the opening/closing section 102 are away from each other, when the wrist USh is inserted into the mount space 101s of the device body 101, the opening/closing section 102 is rotated with respect to the device body 101 and enters the closed state where the device body 101 and the other end of the opening/closing section 102 are adjacent to or in close contact with each other, as indicated by the solid lines in FIG. 2B. Here, the rotation of the opening/closing section 102 may be stopped only at a position set in advance where the opening/closing section 102 enters the closed state, or may be temporarily stopped by a rotation adjusting member provided to the rotating section 103 in a stepwise manner for each predetermined angle or in a non-stepwise manner. As a result, the mount space 101s of the device body 101 is defined, and the inner surface sides (surfaces on the mount space 101s side) of the device body 101 and the opening/closing section 102 come in contact or close contact with the wrist USh, whereby the electronic device 100 is worn on the wrist USh, as shown in FIG. 1C, FIG. 2A, and FIG. 2B. Note that, although not shown, the electronic device 100 may include a lock/unlock mechanism which mutually connects the device body 101 and the other end of the opening/closing section 102 that are adjacent to or in close contact with each other in the closed state indicated by the solid lines in FIG. 2B. As a result, once the electronic device 100 is worn and locked, an accident can be reliably prevented in which the device body 101 and the other end of the opening/closing section 102 become separated from each other and fall off the wrist USh when the electronic device 100 is being used.

(Functional Structure)

The electronic device 100 according to the present embodiment may have the functional structure where it mainly includes, for example, a display section 110, a sensor section 120, an operating section 130, a communicating section 140, a control section 150, a storage section 160, and a power supply section 170, as shown in FIG. 3. In the present embodiment, these sections are incorporated in the above-described device body 101. The inner structure (assembly structure) of the device body 101 will be described later.

The display section 110 is provided extending in a band shape in a substantially center area on the outer surface side of the device body 101 having the curved shape, along the longitudinal direction of the device body 101, as shown in FIG. 1A to FIG. 1C, FIG. 2A, and FIG. 2B. This display section 110 displays, on the outer surface side of the device body 101, the current time, biological information and exercise information acquired during a user operation or during exercise, and the like. As this display section 110, various display panels can be applied, such as those of a liquid-crystal type, a type using a light-emitting element such as an organic EL, and an electronic paper type. Note that the display section 110 may display information in color or monochrome, and may display not only character information and still images but also moving images.

The sensor section 120 has, for example, sensors which acquire biological information such as a pulse rate, body temperature, and blood pressure during a user operation or during exercise, exercise information such as acceleration and angular velocity, physical information such as a geographic position, and environmental information such as barometric pressure, humidity, and geomagnetism. The biological information, exercise information, and the like acquired by the sensor section 120 are stored as sensor data in a predetermined storage region of the storage section 160.

The operating section 130 has operation buttons provided on the outer surfaces of the device body 101 and the opening/closing section 102, and a touch panel switch or the like provided on the view field side (front surface side) of the display section 110. The operating section 130 is used for, for example, a power supply operation for activating the electronic device 100 and an operation for setting various operations of the electronic device 100 (such as the display of the display section 110 and the operation of the sensor section 120).

The communicating section 140 functions as an interface which performs the transmission and reception of acquired sensor data and various signal to and from a device (for example, a smartphone, tablet, personal computer, or the like) and a network outside the electronic device 100. Here, as a method for transmitting and receiving sensor data and the like between the electronic device 100 and the external device or the like via the communicating section 140, various wireless communication methods and wired communication methods can be applied. For example, as a wireless communication method to be applied in the communicating section 140, Bluetooth (registered trademark) which is a short-distance wireless communication standard for digital devices, Bluetooth (registered trademark) low energy (LE) laid out as a low-power-consumption-type communication standard, NFC (Near Field Communication), or Wi-Fi (Wireless Fidelity (registered trademark)) can be favorably applied.

By executing a predetermined program, the control section 150 controls various operations such as a display operation by the display section 110, a sensing operation by the sensor section 120, an operation of transmitting and receiving sensor data and the like by the communicating section 140, a write/read operation by the storage section 160, and a power supply operation by the power supply section 170. The control section 150 may include, for example, a CPU (Central Processing Unit) 11 and a ROM (Read Only Memory).

The storage section 160 stores, for example, sensor data acquired by the sensor section 120. Also, the storage section 160 stores data and information for use or generated in various operations controlled by the control section 150. The storage section 160 may store a program to be executed by the control section 150. Also, the storage section 160 may be in a form of a removable storage medium such as a memory card so that it is removable from the electronic device 100.

The power supply section 170 has a thin curved battery extending in a band shape along the longitudinal direction of the device body 101 having the curved shape, and supplies driving power outputted from the battery to each section of the electronic device 100. Here, as a battery to be applied in the present embodiment, for example, a secondary battery capable of being repeatedly charged and discharged may be applied, such as a lithium-ion battery or a nickel-metal-hydride battery. In this embodiment, the power supply section 170 performs an operation of supplying driving power from the battery to each section and an operation of charging the battery. Note that the power supply section 170 may have a structure where a primary battery such as a commercially-available button-shaped battery or a power supply by an energy harvest technology for generating electricity by energy such as vibrations, light, heat, and electromagnetic waves is used in combination with the above-described secondary battery.

(Assembly Structure/Cross-Sectional Structure)

Next, the assembly structure (inner structure) of the electronic device 100 according to the present embodiment is described.

Figure 4:
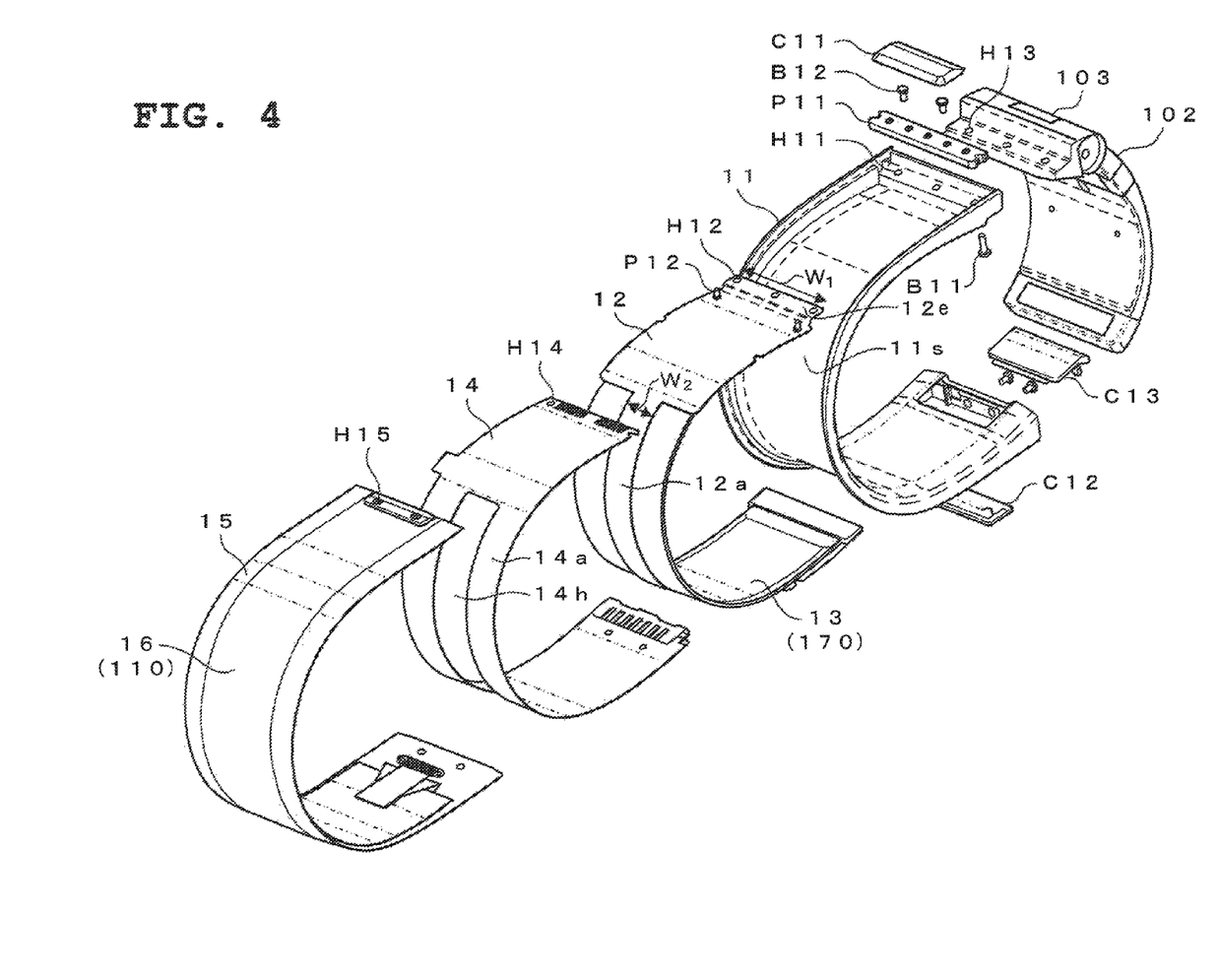
FIG. 4 is an exploded perspective view showing the assembly structure of the electronic device according to the embodiment.
Figure 5A:
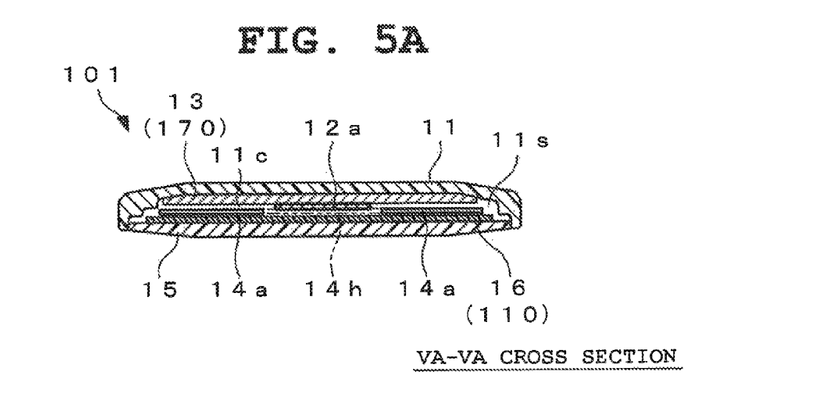
FIG. 5A to FIG. 5C are cross-sectional views of the main portion of the electronic device according to the embodiment.
Figure 5B:
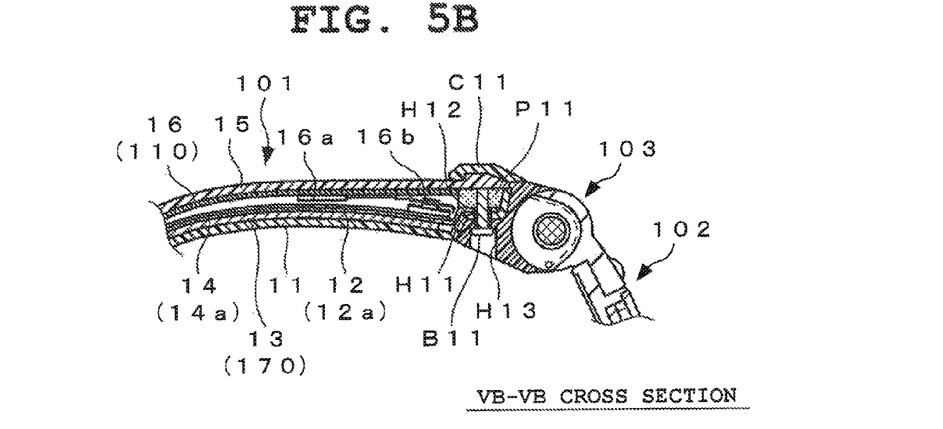
Figure 5C:
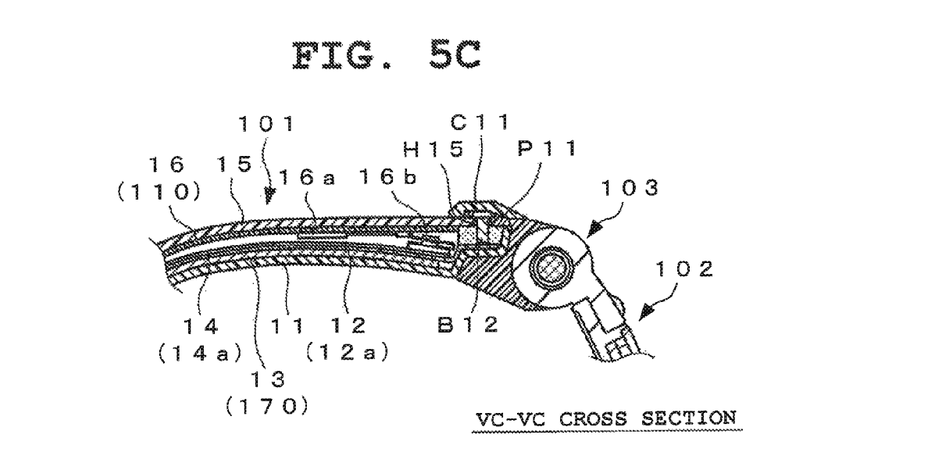

FIG. 4 is an exploded perspective view showing the assembly structure (inner structure) of the electronic device according to the present embodiment. FIG. 5A to FIG. 5C are cross-sectional views of the main portion of the electronic device according to the embodiment. FIG. 5A is a schematic view showing a cross-sectional structure of the electronic device taken along line VA-VA shown in FIG. 1B (for convenience of explanation, in the specification, "V" is used as a symbol corresponding to the Roman numeral "five" in FIG. 1B). FIG. 5B is a schematic view showing a cross-sectional structure of the electronic device taken along line VB-VB shown in FIG. 1B. FIG. 5C is a schematic view showing a cross-sectional structure of the electronic device taken along line VC-VC shown in FIG. 1B. In FIG. 5A to FIG. 5C, in order to clarify the depiction, hatching representing a cross section is partially omitted for convenience.

The device body 101 having the outer appearance shown in FIG. 1A to FIG. 1C mainly includes, for example, a body case 11, a frame 12, a battery 13 (corresponding to the power supply section 170 shown in FIG. 3), a circuit board 14, an exterior cover 15, and a display section 16 (corresponding to the display section 110 shown in FIG. 3), as shown in FIG. 4 and FIG. 5A. This device body 101 has a structure where the frame 12, the battery 13, the circuit board 14, and the display section 16 are incorporated in an accommodation space (accommodating section) 11s formed by the body case 11 and the exterior cover 15.

The body case 11 is formed of a substantially-band-shaped insulating member, and has a shape curved with a predetermined curvature in a longitudinal direction of the band shape, as shown in FIG. 4. Also, the body case 11 has a structure where both side portions are bent or project in one direction (the exterior cover 15 direction in FIG. 4) at least along the longitudinal direction of the band-shaped member. As a result, the body case 11 has a cross section including the recessed accommodating section 11s, as shown in FIG. 4 and FIG. 5A. Also, in the body case 11, at least at one end (end portion on the upper side in FIG. 4) of the band-shaped member in the longitudinal direction, a plurality of holes H11 for connection to the rotating section 103 on the opening/closing section 102 is provided. Note that the body case 11 should preferably has, when the electronic device 100 having at least the frame 12 and the exterior cover 15 mounted in the main body case 11 is worn on a wrist by the user for use, enough rigidity and strength to keep the shape of the accommodating section 11s while allowing deformation to some extent. Also, the body case 11 should preferably has a texture that does not give an uncomfortable feeling when it comes in contact with a human body (skin).

The frame 12 is, for example, formed of a metal thin plate having a band-like flat shape and has a curved shape corresponding to the predetermined curvature of the body case 11, as shown in FIG. 4. Alternatively, the frame 12 has an appropriate rigidity so as to have flexibility and deformability for being curved corresponding to the predetermined curvature, so that the device body 101 is not too warped or deformed by small temporary external force. Also, the frame 12 has a narrow width portion (second frame section) 12a formed by both side portions of an intermediate portion of the band-like thin plate in the width direction except both ends thereof in the longitudinal direction being cut so that the narrow width portion 12a is positioned in an area medially shifted in the width direction by a predetermined length and that the width dimension is narrow, as shown in FIG. 4. In the frame 12, a plurality of mount holes H12 for assembling and fixing inside the accommodating section 11s of the body case 11 are provided at least in a first frame section 12e (end portion on the upper side in FIG. 4) which is one end of the band-like thin plate in the longitudinal direction. In addition, a board fixing pin P12 for defining a mounting position with respect to the circuit board 14 is provided at least on one end of the frame 12 in the longitudinal direction. As the frame 12, for example, a metal material such as iron, stainless steel, aluminum alloy, or the like is adopted. However, the material of the frame 12 is not limited to a metal material as long as an appropriate rigidity can be kept. The first frame section 12e has a width W1 that is larger than the width of the second frame section 12a.

The battery 13 is structured by a battery with a laminate package formed of a resin film, a thin metal package, or the like being formed in a band shape and integrally fixed to one surface side (body case 11 side) of the frame 12, and has a curved shape corresponding to the predetermined curvature, as shown in FIG. 4. Alternatively, the battery 13 has flexibility and deformability of being curved corresponding to the predetermined curvature. Here, the battery 13 has a band-like flat shape with dimensions including a substantially entire area of the frame 12, and is mounted in the substantially entire area on one surface side of the frame 12, as shown in FIG. 4. Accordingly, in an area where the second frame section 12a of the frame 12 is formed, the battery 13 is exposed on both sides of the second frame section 12a. Note that, although not shown, an output terminal of the battery 13 is electrically connected to the circuit board 14 and the display section 16 in, for example, areas corresponding to both sides of the frame 12 in the longitudinal direction.

The circuit board 14 has a functional component mount section (first board region) where the communicating section 140, the control section 150, the storage section 160, and the like described in the Functional Structure section above are mounted and a pattern forming section (second board area) where only a wiring pattern such as signal wiring or antenna wiring is formed. This circuit board 14 is formed of, for example, an insulating board having a band-like flat shape with dimensions corresponding to the substantially entire area of the frame 12 and the battery 13 described above, and has a functional component mount section provided in both ends of the band shape in the longitudinal direction and a pattern forming section provided to its intermediate portion except both ends, as shown in FIG. 4. In the circuit board 14 having at least the pattern forming section, a thin-film or film-shaped thin insulating board such as a flexible printed circuit board (FPC) is formed in a band shape, and has a curved shape corresponding to the predetermined curvature, as shown in FIG. 4. Alternatively, the circuit board 14 has flexibility and deformability of being curved corresponding to the predetermined curvature. Also, in the circuit board 14 where the pattern forming section is provided, an opening 14h of which the substantially center portion have been cut off by a predetermined length in the width direction and which is extending in the longitudinal direction is provided to an intermediate portion of the band shape except both ends thereof in the longitudinal direction, as shown in FIG. 4. That is, the circuit board 14 has a structure where both ends in the longitudinal direction are connected by two narrow width sections (first circuit board sections) 14a formed on both sides of the opening 14h in the width direction. Here, the width dimension of the opening 14h provided in the circuit board 14 is set to be larger than the width dimension of the second frame section 12a provided to the frame 12. Accordingly, as will be described below, the second frame section 12a of the frame 12 is formed to be positioned between the first circuit board sections 14a forming the opening 14h of the circuit board 14, with a unit formed of the frame 12, the battery 13, and the circuit board 14 being substantially in close contact with each other and mounted in the body case 11, as shown in FIG. 5A. That is, since the second frame section 12a of the frame 12 and the first circuit board sections 14a of the circuit board 14 are formed such that they do not overlap with each other in a plane when viewed from the laminated direction of the frame 12 and the circuit board 14 (viewed from a diagonally forward left direction in FIG. 4 or viewed from below in FIG. 5A), even if the device body 101 is warped or deformed, the first circuit board sections 14a of the circuit board 14 do not come in contact with the second frame section 12a of the frame 12. Also, even if the battery 13 expands with time and presses the second frame section 12a toward the circuit board 14, since the second frame section 12a of the frame 12 is in the accommodating section 11s in the opening 14h, the first circuit board sections 14a do not come in contact with the second frame section 12a of the frame 12. Also, in at least one end of the circuit board 14 in the longitudinal direction (end on the upper side in FIG. 4), a positioning hole H14 for defining a mounting position with respect to the frame 12 is provided. In the first circuit board sections 14a where the pattern forming section is provided, a wiring pattern is formed, such as a sensor signal line for transmitting a detection signal outputted from the sensor section 120 to the control section 150, a power supply line for supplying driving power supplied from the power supply section 170 to each structure, and an antenna wiring in accordance with a wireless communication method applied in the communicating section 140. Here, by forming a sensor signal line on one of the two first circuit board sections 14a forming the opening 14h and a power supply line on the other one, and then separating them by the opening 14h, it is possible to favorably transmit a subtle detection signal outputted from the sensor section 120 to the control section 150 while inhibiting the influences of a magnetic field occurred on the power supply line. Note that the circuit board 14 may be structured such that the above-described functional component and wiring pattern are mounted or formed only on one surface side of the insulating board, or may be structured such that the functional component and wiring pattern are mounted or formed on both front and back surface sides. Here, the functional component and wiring pattern mounted or formed on the circuit board 14 are covered by a known insulating protection film for protection.

The exterior cover 15 is, for example, formed of an insulating thin plate having a band-like flat shape, and has a curved shape corresponding to the curved shape of the body case 11, as shown in FIG. 4. Alternatively, the exterior cover 15 has flexibility and deformability of being curved corresponding to the curved shape of the body case 11. Also, the exterior cover 15 is mounted such that it closes and seals the open end side (lower side in the drawing) of the accommodating section 11s provided in the body case 11, as shown in FIG. 5A. Here, the exterior cover 15 has characteristics (such as rigidity, resistance to heat, resistance to moisture, and resistance to chemical agents) by which each section accommodated in the accommodating section 11s can be protected against at least pressure from outside (external pressure) and surrounding environments (such as temperature, moisture, and chemical agents) of the electronic device 100. Also, in the present embodiment, the exterior cover 15 is formed of, for example, a transparent resin material or glass material, and has a structure in which the display section 16 described later is integrally provided on one surface side (accommodating section 11s side) of the exterior cover 15. As a result, information displayed on the display section 16 is transmitted via the transparent exterior cover 15 to the view field side, and thereby visually recognized by a user US. Also, in the exterior cover 15, a plurality of mount holes H15 for closing the accommodating section 11s of the body case 11 are provided in at least one end (end on an upper side in FIG. 4) of the band-shaped thin plate in the longitudinal direction.

The display section 16 is structured by, for example, a thin display device being formed to have a band-like flat shape and integrally provided on one surface (accommodating section 11s side) of the exterior cover 15, and has a curved shape corresponding to the curved shape of the exterior cover 15, as shown in FIG. 4. Alternatively, the display section 16 has flexibility and deformability corresponding to the curved shape of the exterior cover 15. This display section 16 is a display panel that can maintain display even if it is being warped or deformed, such as a liquid-crystal display panel having liquid crystal filled between flexible film resin boards, an organic EL display panel having a flexible film resin board provided with an organic EL layer, or an electronic paper display panel having color particles filled between flexible film resin boards. Information displayed on the display section 16 is transmitted to the user's view field side via the transparent exterior cover 15 for visual recognition. Although not shown in the drawings, a driver IC of the display section 16 is provided at one end of the display section 16 or the exterior cover 15 in the longitudinal direction, and is electrically connected nearby to the circuit board 14 and the battery 13.

The opening/closing section 102 has a structure in which, for example, the rotating section 103 is provided at one end (end portion on the upper side in FIG. 4) of the substantially-band-shaped member in the longitudinal direction, as shown in FIG. 4. The rotating section 103 includes a rotating shaft, and formed such that the opening/closing section 102 rotates with the rotating shaft as a supporting point. This rotating section 103 is provided with a plurality of mount holes H13 for connection with at least the device body 101.

(Example of Assembling Procedure)

Next, an assembling procedure for the above-described electronic device is described with reference to FIG. 4 and FIG. 5A to FIG. 5C. First, the mount holes H13 provided in the rotating section 103, the mount holes H11 provided in the body case 11, and the mount holes H12 provided in the frame 12 are aligned in position, and male screws are inserted from the inner side (mount space 101s side; lower side in FIG. 5B) of the body case 11 and the rotating section 103 so as to be screwed into female screws provided in a holder P11 and fixed, as shown in FIG. 4 and FIG. 5B. As a result, the frame 12 and the battery 13 integrally provided on the frame 12 are mounted in the accommodating section 11s of the body case 11 with them being curved.

Next, a board fixing pin P12 provided on the frame 12 is fitted into the positioning hole H14 provided in the circuit board 14 to define the mounting position of the circuit board 14 with respect to the frame 12. Then, ends of the frame 12 and the circuit board 14 in the longitudinal direction are bonded and fixed together with, for example, an adhesive, double-sided adhesive tape, or the like. As a result, the circuit board 14 having various functional components mounted therein is mounted in the accommodating section 11s of the body case 11 with it being curved and substantially in close contact with the frame 12. Also, in an area corresponding to the ends of the frame 12 and the circuit board 14 in the longitudinal direction, the battery 13 and the circuit board 14 are electrically connected to each other.

Note that, as a method for positioning and fixing the frame 12 and the circuit board 14, a method of fixing with screws, a method of welding with resin, or a hot melt coating method can be adopted, in addition to the method using an adhesive or double-sided adhesive tape.

Next, the exterior cover 15 having the display section 16 integrally provided thereon is arranged to close the accommodating section 11s of the body case 11, and male screws B12 are inserted from the outer side (upper side in FIG. 4 and FIG. 5C) into the mount holes H15 provided in the exterior cover 15 so as to be screwed into female screws provided in the holder P11 and fixed, as shown in FIG. 4 and FIG. 5C. As a result, the frame 12, the battery 13, and the circuit board 14 are assembled together, and the accommodating section 11s of the body case 11 having the display section 16 accommodated therein is sealed. Here, in an area corresponding to ends of the exterior cover 15 and the circuit board 14 in the longitudinal direction, a driver IC 16a of the display section 16 provided on the exterior cover 15 side, a connector 16b of the circuit board 14, and the battery 13 are electrically connected together via a flat cable, a spring-based electrode terminal, or the like.

Then, a cover component C11 is mounted to cover the peripheries of the male screws B12 and the mount holes H15 used for screwing and fixing the exterior cover 15 to the body case 11 via the holder P11. As a result, moisture intrusion and the like into the sealed accommodating section 11s of the body case 11 is prevented, and the design quality of the electronic device 100 is enhanced. In FIG. 4, FIG. 5B, and FIG. 5C, for convenience of depiction, only one end of the device body 101 to which the rotating section 103 is connected (end on the upper side in FIG. 4) has been described in detail. However, similar assembly may be performed on the other end (end on the lower side in FIG. 4) so as to fix both ends of the frame 12, the circuit board 14, and the exterior cover 15 to the body case 11. Note that the reference numeral C12 in FIG. 4 denotes a cover component which covers the periphery of male screws (omitted in the drawing) for fixing the other end of the exterior cover 15 to the body case 11, and the reference numeral C13 denotes another cover component mounted on the other end of the body case 11.

Next, operations and effects of the electronic device according to the present embodiment are described.

Figure 6A:
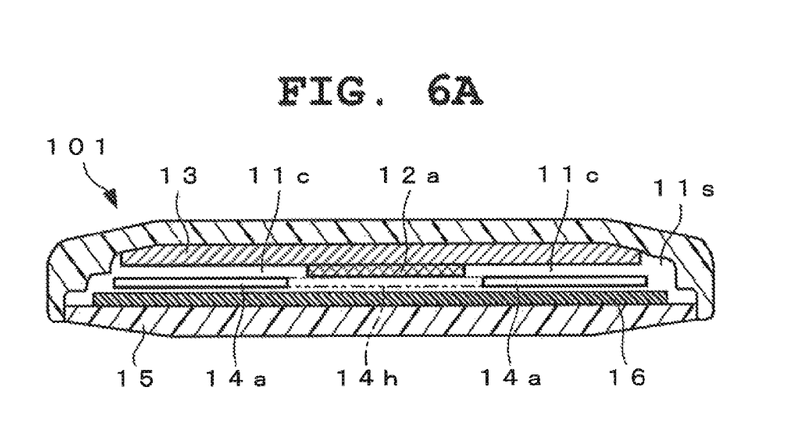
FIG. 6A and FIG. 6B are schematic cross-sectional views for describing operations and effects of the electronic device according to the embodiment.
Figure 6B:
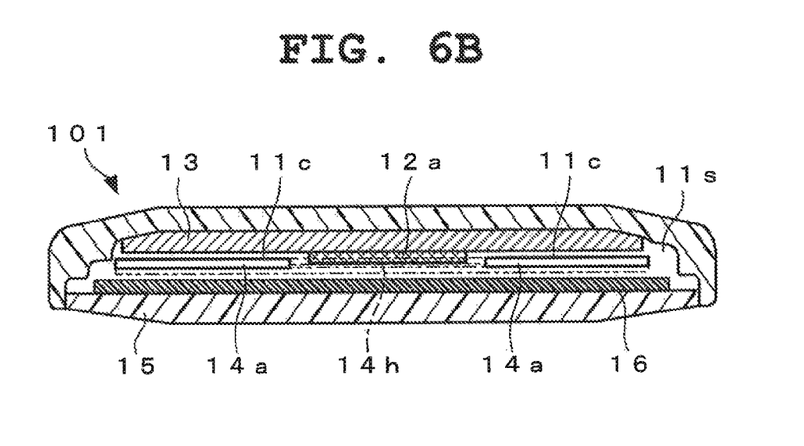

FIG. 6A and FIG. 6B are schematic cross-sectional views for describing operations and effects of the electronic device according to the present embodiment. Here, the operations and effects are described based on the cross-sectional view shown in FIG. 5A.

As described in the Related Art section, wristband-type electronic devices to be worn on a wrist, an arm, or the like are required to be thin and have a curved shape with a predetermined curvature. In order to achieve this type of electronic device, a circuit board incorporated in the device may have a structure using a flexible FPC. In this case, since the rigidity and strength of the circuit board itself are low, warpage and deformation easily occur by external pressure applied at the time of manufacturing or using the electronic device, which may cause various functional components and structural members incorporated therein to come in contact with the circuit board and be damaged or exfoliated.

The electronic device 100 according to the present embodiment is formed of a thin plate having some rigidity and strength, includes the frame 12 having a curved shape corresponding to a predetermined curvature, and has a structure where the battery 13 and the circuit board 14 are integrally or partially fixed to the frame 12. Specifically, the electronic device 100 has a structure in which the battery 13 constituted by a secondary battery is integrally fixed to one surface side of the frame 12, and the circuit board 14 having the functional components such as the communicating section 140, the control section 150, and the storage section 160 mounted therein is fixed to the other surface side (exterior cover 15 side) of the frame 12 such that both ends are fixed, as shown in FIG. 4 and FIG. 5A to FIG. 5C. That is, the arrangement areas of the battery 13 and the circuit board 14 are each defined (determined) by the frame 12, and the battery 13 and the circuit board 14 are arranged to interpose the frame 12 and come close contact with both sides thereof, as shown in FIG. 5A. As a result, according to the present embodiment, warpage and deformation by external pressure applied at the time of manufacturing or using the electronic device can be inhibited, and damage, exfoliation, and the like of the incorporated functional components can be inhibited.

In addition, the electronic device according to the present embodiment has a structure in which the second frame section 12a extending in the longitudinal direction is provided to the intermediate portion of the frame 12 except both ends thereof, and the opening 14h extending in the longitudinal direction and two first circuit board sections 14a extending along both side portions in the longitudinal direction (or both side of the opening 14h) are provided to the intermediate portion of the circuit board 14 excluding both ends thereof fixed to the frame 12, as shown in FIG. 4. Here, the opening 14h is provided in an area corresponding to the second frame section 12a provided to the frame 12, and is set to have a width dimension larger than that of the second frame section 12a.

Also, in the present embodiment, when a unit where the battery 13 and the circuit board 14 have been laminated to be integrally or partially fixed to the frame 12 is mounted in the body case 11, the second frame section 12a of the frame 12 is positioned between the first circuit board sections 14a forming the opening 14h of the circuit board 14, in an intermediate area between the frame 12 and the circuit board 14, whereby the first circuit board sections 14a are separated from each other as shown in FIG. 5A. In the intermediate area between the frame 12 and the circuit board 14, a space 11c is formed between the battery 13 provided on one surface side of the frame 12 and the first circuit board sections 14a of the circuit board 14 provided on the other surface side of the frame 12, which can be recognized when the device body 101 is viewed in a thickness direction (vertical direction in FIG. 5A). This space 11c is formed by positioning and fixing both ends of the circuit board 14 with respect to the frame 12. In addition, this space 11c is set to prevent the frame 12 and the circuit board 14 from coming in contact with each other due to a dimensional difference occurred by a curvature difference by a subtle change of the peripheral length of each of the frame 12 and the circuit board 14 caused by at least manufacturing variation and work variation at the time of assembling components and members forming the electronic device and warpage or deformation at the time of using the electronic device.

As described above, in the present embodiment, the battery 13 and the circuit board 14 are laminated and fixed to the frame 12, and the second frame section 12a and the first circuit board sections 14a formed at the intermediate portions of the frame 12 and the circuit board 14 except both ends thereof are arranged such that they are separated from each other so as not to overlap with each other in a planar view when viewed from the laminated direction of the frame 12 and the circuit board 14. In addition, the first circuit board sections 14a of the circuit board 14 are formed having the predetermined space 11c so as to prevent contact with the battery 13. Accordingly, when the structure according to the present embodiment is applied in a thin electronic device having a curved shape with a predetermined curvature, the following operations and effects are provided.

That is, in order to address a dimensional difference occurred due to manufacturing variation and work variation of components and members or external pressure applied at the time of using the electronic device 100, the second frame section 12a of the frame 12 enters the opening 14h of the circuit board 14 when the frame 12, the circuit board 14, the battery 13, and the like are mounted in the device body 101, and thereby prevents the second frame section 12a and the first circuit board sections 14a from coming in contact with each other, as shown in FIG. 6A and FIG. 6B. Here, the space 11c formed between the circuit board 14 and the battery 13 is ensured to the extent that the space 11c is not lost. Thus, according to the present embodiment, the variation and dimensional difference described above can be absorbed, the occurrence of damage, exfoliation, and the like of the components and members at the time of manufacturing and using the electronic device can be prevented, and favorable manufacturing quality can be achieved.

In the present embodiment, a secondary battery such as a lithium-ion battery has been adopted as the battery 13 for supplying driving current to each section of the electronic device. However, it is known that the housing of this type of battery is expanded at the time of charging or due to deterioration with time. Accordingly, in the present embodiment, the second frame section 12a and the first circuit board sections 14a are arranged to be separated from each other so as not to come in contact with each other, in the intermediate portions of the frame 12 and the circuit board sections 14 except both ends thereof, and the space 11c is formed between the battery 13 and the first circuit board sections 14a of the circuit board 14. Therefore, expansion that occurs to the battery 13 can be absorbed by the space 11c, whereby contact and interference among the components and members incorporated in the device body 101 can be prevented, and favorable product quality can be achieved.

MODIFICATION EXAMPLES

Next, modification examples of the above-described electronic device according to the embodiment will be described.

In the above-described embodiment, a metal thin plate curved corresponding to the curvature of the body case 11 is applied as the frame 12 mounted in the body case 11 of the device body 101 forming the electronic device 100. Here, in the present invention, novel operations and effects can be further acquired by structuring the frame as in the following modification examples.

That is, in portable devices and information devices in recent years, the computation processing speed of a control section has been increased along with the sophistication of the functionality and the performance. Accordingly, the quantity of heat generated inside these devices also increases. Further, most of the portable devices in recent years have a communicating function, and a function for transmitting and receiving data to and from an external device and operating in conjunction with the external device, which have become indispensable functions. In view of these circumstances, the present embodiment has the following modification examples.

A first modification example of the electronic device according to the present embodiment has a structure in which, among the functional components and the like mounted on the circuit board 14 described above, a portion or functional component mount section where heat is generated by an operation or an area nearby is connected and fixed to the frame 12 on the back surface side (frame 12 side) of the circuit board 14. Here, the circuit board 14 and the frame 12 are connected and fixed preferably by using a highly thermally-conductive material. For example, a structure can be adopted in which a highly thermally-conductive adhesive or heat-conductive sheet is interposed therebetween. As a result of this structure, heat generated on the circuit board 14 can be favorably transmitted to the frame 12 and diffused, and an increase in the internal temperature of the electronic device 100 can be inhibited.

A second modification example of the electronic device according to the present embodiment has a structure in which the frame 12 to be mounted in and fixed to the body case 11 in the above-described first modification example is divided in the longitudinal direction into, for example, two (or more) sides including a heat source side and a cooling side and each side is connected together with a heat pipe. As a result of this structure, heat transmission and diffusion between two sides of the divided frame 12 can be promoted, and an increase in the internal temperature of the electronic device 100 can be inhibited.

A third modification example of the electronic device according to the present embodiment has a structure in which a highly thermally-conductive member such as an aluminum alloy or a copper alloy is applied as the above-described frame 12, and a portion of the frame 12 is extended and exposed from the body case 11 and the exterior cover 15 constituting the device body 101 so as to make contact with outside air. Note that, here, one portion of the frame 12 may be exposed, or a plurality of portions thereof may be exposed. The exposed portion should preferably be arranged such that the exposed frame 12 does not directly come in contact with the human body (user's body). By the frame 12 being used as a heat-dissipating plate, heat generated inside the device can be favorably dissipated outside the electronic device 100, and an increase in the internal temperature can be inhibited.

A fourth modification example of the electronic device according to the present embodiment has a structure in which antenna wiring corresponding to a wireless communication method applied to the communicating section 140 is arranged in the second frame section 12a provided to the frame 12 described above. Here, no circuit components and the like are mounted around the second frame section 12a provided to the frame 12 and noise occurs less. Therefore, the radio wave environment is in a relatively favorable state. As a result, favorable communication with a device outside the electronic device can be achieved.

A fifth modification example of the electronic device according to the present embodiment has a structure in which a material having flexibility to some extent is applied as the above-described frame 12. As a result of this structure, a close contact with the human body when the electronic device 100 is worn can be ensured, and the warpage and deformation of the electronic device 100 by external force can be inhibited, whereby damage, exfoliation, and the like of the incorporated components and members can be inhibited.

A sixth modification example of the electronic device according to the present embodiment has a structure in which a shape memory alloy having a shape retention characteristic at normal temperature is applied as the above-described frame 12. As a result of this structure, when the electronic device 100 is worn for use at normal temperature, counterforce (resistance) to warpage and deformation of the electronic device 100 by external force can be provided.

A seventh modification example of the electronic device according to the present embodiment has a structure in which a shape memory alloy having a shape recovery property by heat is applied as the above-described frame 12. As a result of this structure, even if warpage or deformation occurs to the electronic device 100 by external force, its shape can be restored by body temperature when the electronic device 100 is worn, or the like.

In the above-described embodiment, the structure has been described in which the frame 12 made of a metal material such as iron, stainless, aluminum alloy, or the like is applied. However, the present invention is not limited thereto. In the present invention, a non-metal material or structure having a certain level of strength may be applied, or a highly thermally-conductive member may be applied.

Also, in the above-described embodiment, the structure has been described in which one second frame section 12a is provided to the intermediate portion of the frame 12 except both ends thereof, and the opening 14h formed of two first circuit board sections 14a is provided to the intermediate portion of the circuit board 14 except both ends thereof. However, the present invention is not limited thereto. That is, as described in the descriptions of the operations and effects, the present invention may have another structure as long as manufacturing variation and work variation of components and members and a dimensional difference occurring due to external pressure applied at the time of using the electronic device 100 can be absorbed by the shapes and arrangement of the frame 12 and circuit board 14 and the space. For example, the present invention may have a structure in which the frame 12 has an opening formed of two second frame sections at an intermediate portion of the frame except both ends thereof and the circuit board 14 is provided with one first circuit board section at an intermediate portion of the circuit board except both ends thereof, or may have a structure in which one first circuit board section is provided to an intermediate portion of each of the frame and the circuit board except both ends thereof.

Moreover, in the above-described embodiment, the electronic device 100 includes the display section 110 which displays various information. However, the present invention is not limited thereto. That is, the present invention may be applied in an electronic device which does not include the display section 110 and has only a function for accumulating sensor data acquired from the sensor section 120 in the storage section 160. In this case, the exterior cover 15 has only function for protecting the circuit board 14, the battery 13, and the like incorporated in the device body 101 against external pressure or surrounding environments.

Furthermore, in the above-described embodiment, the electronic device 100 is worn on a wrist of a human body. However, the present invention is not limited thereto. That is, the present invention can be favorably worn not only on a wrist or arm but also on a portion having a predetermined curvature such as an ankle and used. Still further, the target of the present invention is not limited to the human body, and may be applied to a collar-type device or the like for acquiring, for example, biological information or physical information or a pet.

While the present invention has been described with reference to the preferred embodiments, it is intended that the invention be not limited by any of the details of the description therein but includes all the embodiments which fall within the scope of the appended claims.

What is claimed is:

1. An electronic device comprising:
   a body case which has an accommodating section at least partially in a curved shape;
   a frame which has a first frame section and a second frame section having a width that is narrower than a width of the first frame section, the frame being accommodated in the accommodating section; and
   a circuit board which is accommodated in the accommodating section so as to be laminated on the frame, wherein a part of the circuit board is superposed on the first frame section, and the circuit board is not superposed on the second frame section.

2. The electronic device according to claim 1, wherein the circuit board comprises an opening section having a width that is wider than the width of the second frame section, and a first circuit board section positioned at least on one side of the opening section in a width direction.

3. The electronic device according to claim 2, wherein the second frame section is provided to an intermediate portion of the frame excluding both ends in a longitudinal direction, and the first circuit board section is provided to an intermediate portion of the circuit board excluding both ends in the longitudinal direction.

4. The electronic device according to claim 2, wherein the circuit board has at least a first board area where a functional component is mounted and a second board area where only a predetermined wiring pattern is provided, and
   wherein the second board area is set on the first circuit board section.

5. The electronic device according to claim 4, wherein the second board area is provided with one or more of (i) a signal line through which a predetermined signal is transmitted, (ii) a power supply line for supplying electric power for driving the functional component, and (iii) an antenna line for transmission and reception of a predetermined radio wave in the functional component.

6. The electronic device according to claim 1, wherein the frame has a material characteristic by which the curved shape is recovered even when external pressure is applied to at least the body case.

7. The electronic device according to claim 1, further comprising:
   a battery arranged on one surface side of the frame,
   wherein the circuit board is arranged on the other surface side of the frame.

8. The electronic device according to claim 7, wherein a predetermined space is provided at least between the circuit board and the battery.

9. The electronic device according to claim 2, wherein the frame and the circuit board are accommodated in the accommodating section such that the second frame section is positioned in the opening.

10. The electronic device according to claim 1, wherein the circuit board and the second frame section are flexible and deformable, and arranged so as not to overlap each other when viewed from a laminated direction of the frame, even when the shape of the curved shape is deformed.

11. The electronic device according to claim 1, wherein the frame has a narrow width portion formed by both side portions of an intermediate portion of a band-like thin plate in a width direction, except both ends in a longitudinal direction, being cut so that the narrow width portion is positioned in an area medially shifted in a width direction by a predetermined length and that a width dimension of the narrow width portion is narrow.

12. The electronic device according to claim 1, wherein the circuit board comprises an opening section having a width that is wider than the width of the second frame section, and a first circuit board section positioned on both sides of the opening section in a width direction.

13. The electronic device according to claim 12, wherein a sensor signal line is formed on one of sides of the first circuit board sections and a power supply line is formed on the other side, and the sensor signal line and the power supply line are separated from each other by the opening section.

* * * * *